United States Patent
Chen et al.

(10) Patent No.: US 11,752,177 B2
(45) Date of Patent: *Sep. 12, 2023

(54) METHOD OF REDUCING TOBACCO ADDICTION IN SMOKING SUBJECT WITH LACTOBACILLUS FERMENTUM GKF3

(71) Applicant: GRAPE KING BIO LTD, Taiwan (CN)

(72) Inventors: Chin-Chu Chen, Taiwan (CN); Yen-Lien Chen, Taiwan (CN); Shih-Wei Lin, Taiwan (CN); Yen-Po Chen, Taiwan (CN); Ci-Sian Wang, Taiwan (CN); Yu-Hsin Hou, Taiwan (CN); Yang-Tzu Shih, Taiwan (CN); Ching-Wen Lin, Taiwan (CN); Ya-Jyun Chen, Taiwan (CN); Jia-Lin Jiang, Taiwan (CN); You-Shan Tsai, Taiwan (CN); Zi-He Wu, Taiwan (CN)

(73) Assignee: GRAPE KING BIO LTD, Taiwan (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/554,626

(22) Filed: Dec. 17, 2021

(65) Prior Publication Data

US 2023/0128854 A1 Apr. 27, 2023

(30) Foreign Application Priority Data

Oct. 22, 2021 (TW) .......................... TW110139393

(51) Int. Cl.
*A61P 25/34* (2006.01)
*C12N 1/20* (2006.01)
(Continued)

(52) U.S. Cl.
CPC .......... *A61K 35/742* (2013.01); *A61K 9/0053* (2013.01); *A61P 25/34* (2018.01); *C12N 1/205* (2021.05); *C12R 2001/225* (2021.05)

(58) Field of Classification Search
CPC ....... A61K 9/0053; A61P 25/34; C12N 1/205; C12R 2001/225
See application file for complete search history.

(56) References Cited

U.S. PATENT DOCUMENTS

2020/0155623 A1* 5/2020 Chen ...................... A23L 29/065
2021/0069269 A1* 3/2021 Feuz ........................ A61P 25/34

FOREIGN PATENT DOCUMENTS

| CN | 105891357 A | 8/2016 |
| CN | 112334145 A | 2/2021 |

(Continued)

OTHER PUBLICATIONS

Oh, Jongwon, et al. "A Simple and High-Throughput LC-MS-MS Method for Simultaneous Measurement of Nicotine, Cotinine, 3-OH Cotinine, Nornicotine and Anabasine in Urine and Its Application in the General Korean Population." Journal of Analytical Toxicology 46.1 (2022): 25-36. (Year: 2020).*

(Continued)

*Primary Examiner* — Lora E Barnhart Driscoll
*Assistant Examiner* — Candice Lee Swift
(74) *Attorney, Agent, or Firm* — Hayes Soloway PC (57) ABSTRACT

The present invention is related to a method of reducing tobacco addiction in a smoking subject with *Lactobacillus fermentum* GKF3, including daily administering an oral composition containing the *Lactobacillus fermentum* GKF3 to the smoking subject, in which the oral composition reduces the total amount of the nicotine metabolites in urine.

12 Claims, 3 Drawing Sheets

Specification includes a Sequence Listing.

(51) Int. Cl.
*A61K 9/00* (2006.01)
*C12R 1/225* (2006.01)
*A61K 35/742* (2015.01)

(56) References Cited

FOREIGN PATENT DOCUMENTS

WO WO-2008138571 A1 * 11/2008 ........... A61K 31/465
WO 2019202033 A1 10/2019

OTHER PUBLICATIONS

Jed E. Rose, "Nicotine and nonnicotine factors in cigarette addiction", Journal, 2006, 274-285, vol. 184, Psychopharmacology.

Anonymous, "Medicines that Help you Quit Smoking—Four stages of nicotine replacement therapy", 2014, webpage <https://www.e-quit.org/CustomPage/HtmlEditorPage.aspx?MId=666&ML=1> (Retrieved on May 26, 2023).

Bhavika Chauhan and Nileshkumar Pandya,, "Isolation and Characterization of Nicotine Reducing Probiotics", International Journal of Current Microbiology and Applied Sciences, 2019, vol. 8, Issue 7, pp. 1193-1200, 8 pages.

Gulhane et al., "Degradation of Nicotine by the Resident Flora of the Oral Cavity in Tobacco Consumers", International Journal of Current Microbiology and Applied Sciences, 2016, vol. 5, Issue 12, pp. 365-369, 5 pages.

* cited by examiner

METHOD OF REDUCING TOBACCO ADDICTION IN SMOKING SUBJECT WITH LACTOBACILLUS FERMENTUM GKF3

RELATED APPLICATION

This application claims priority to an earlier Taiwan Application Serial Number 110139393, filed Oct. 22, 2021, which is incorporated herein by reference in its entirety.

REFERENCE MATERIALS

A sequence listing is being submitted herein as an ASCII text file with the name "SP_5536_US_SEQ_LIST_ASCII.txt", created on Jan. 21, 2022, with a file size of 2141 bytes.

BACKGROUND

Field of Invention

The present invention is related to a method of reducing tobacco addiction. More practically, the present invention is related to a method of reducing tobacco addition in a smoking subject with *Lactobacillus fermentum* GKF3.

Description of Related Art

A burnt tobacco can emit more than 7,000 chemicals, including more than 90 known cancerogens. These chemicals cause harm to the body of a smoker and to the health of others. However, it is hard for the smoker to quit smoking because nicotine in the tobacco is addictive. When the smoker smokes, nicotine can be transferred to brain from lungs through blood within several seconds so that the smoker feels excitement and/or joy. Once the amount of nicotine in blood decreases, the smoker is very likely to suffer from withdrawal symptoms of nicotine, such as anxiety, irritability, impaired concentration, depression, insomnia, cough and headache. Moreover, the brain develops tolerance to nicotine, and consequently, the smoker needs more smoking amount to relieve the withdrawal symptoms of nicotine.

Currently, the commercially available smoking cessation drugs help the smokers quit smoking by relieving the withdrawal symptoms of nicotine, and the smoking cessation drugs can be divided into nicotine replacement drugs and non-nicotine replacement drugs. The nicotine replacement drugs provide low-dose nicotine for the smokers in different dosage forms (lozenge, inhalant, nasal spray and/or patch) and can gradually reduce dependence of the smokers on nicotine by stepwise adjustment of the dose. The non-nicotine replacement drugs can not only relieve the withdrawal symptoms of nicotine triggered by a reduced smoking amount but also reduce the feelings of excitement and/or joy brought by smoking. However, these smoking cessation drugs cause many side effects.

In view of this, it is urgent to provide an oral composition capable of reducing tobacco addiction with few side effects to solve the aforementioned problems.

SUMMARY

Therefore, one aspect of the present invention provides a method of reducing tobacco addiction in a smoking subject with *Lactobacillus fermentum* GKF3, in which the method can include but not limited to daily administering to the smoking subject an oral composition containing an effective dosage of *Lactobacillus fermentum* GKF3.

Another aspect of the present invention provides a method of reducing tobacco addiction in a smoking subject with *Lactobacillus fermentum* GKF3, in which the method can include but not limited to daily administering to the smoking subject an oral composition containing an effective dosage of *Lactobacillus fermentum* GKF3, and the effective dosage can be 700 mg/60 kg body weight (bw)/day to 900 mg/60 kg bw/day, for example.

The other aspect of the present invention provides a method of reducing tobacco addiction in a smoking subject with *Lactobacillus fermentum* GKF3, in which the method can include but not limited to daily administering to the smoking subject an oral composition containing an effective dosage of *Lactobacillus fermentum* GKF3 as an active ingredient, and the effective dosage can be $10^{10}$ colony forming unit (CFU)/60 kg bw/day to $10^{12}$ CFU/60 kg bw/day, for example.

According to the aforementioned aspect of the present invention, a method of reducing tobacco addiction in a smoking subject with *Lactobacillus fermentum* GKF3 is provided. The method can include but not limited to daily administering to the smoking subject an oral composition containing an effective dosage of *Lactobacillus fermentum* GKF3 as an active ingredient, in which the *Lactobacillus fermentum* GKF3 can be deposited in China General Microbiological Culture Collection Center (CGMCC) with an accession number CGMCC 15203 on Jan. 12, 2018, for example. The deposit has been made under the terms of the Budapest Treaty.

In one embodiment of the present invention, the effective dosage can be 700 mg/60 kg bw/day to 900 mg/60 kg bw/day, for example. In one embodiment of the present invention, the effective dosage can be $10^{10}$ colony forming unit (CFU)/60 kg bw/day to $10^{12}$ CFU/60 kg bw/day, for example. In one embodiment of the present invention, the oral composition reduces the total amount of nicotine metabolites in the urine of the smoking subject daily administered with the oral composition when compared to a corresponding smoking subject not administered with the oral composition. In one embodiment of the present invention, the nicotine metabolites can include but not limited to cotinine and/or trans-3-hydroxycotinine. In one embodiment of the present invention, the total amount of the nicotine metabolites can be reduced by 10 ng/mL to 1,100 ng/mL, for example. In one embodiment of the present invention, the oral composition is daily administered to the smoking subject for an administration period, and the administration period can be 25 days to 30 days, for example.

According to another aforementioned aspect of the present invention, a method of reducing tobacco addiction in a smoking subject with *Lactobacillus fermentum* GKF3 is provided. The method can include but not limited to daily administering to the smoking subject an oral composition containing an effective dosage of *Lactobacillus fermentum* GKF3, in which an accession number of *Lactobacillus fermentum* GKF3 can be CGMCC 15203, for example, and the effective dosage can be 700 mg/60 kg bw/day to 900 mg/60 kg bw/day, for example.

In one embodiment of the present invention, the oral composition reduces the total amount of nicotine metabolites in urine of the smoking subject daily administered with the oral composition when compared to a corresponding smoking subject not administered with the oral composition. In one embodiment of the present invention, the nicotine metabolites can include but not limited to cotinine and/or trans-3-hydroxycotinine. In one embodiment of the present invention, the total amount of nicotine metabolites can be reduced by 10 ng/mL to 1100 ng/mL, for example. In one embodiment of the present invention, the oral composition is daily administered to the smoking subject for an administration [[time]]period, and the administration period can be 25 days to 30 days, for example.

According to the other aforementioned aspect of the present invention, a method of reducing tobacco addiction in a smoking subject with *Lactobacillus fermentum* GKF3 is provided. The method can include but not limited to daily administering to the smoking subject an oral composition containing an effective dosage of *Lactobacillus fermentum* GKF3, in which an accession number of *Lactobacillus fermentum* GKF3 can be CGMCC 15203, for example, and the effective dosage can be $10^{10}$ CFU/60 kg bw/day to $10^{12}$ CFU/60 kg bw/day, for example.

In one embodiment of the present invention, the oral composition reduces the total amount of nicotine metabolites in urine of the smoking subject daily administered with the oral composition when compared to a corresponding smoking subject not administered with the oral composition. In one embodiment of the present invention, the nicotine metabolites can include but not limited to cotinine and/or trans-3-hydroxycotinine. In one embodiment of the present invention, the total amount of nicotine metabolites can be reduced by 10 ng/mL to 1100 ng/mL, for example. In one embodiment of the present invention, the oral composition is daily administered to the smoking subject for an administration period, and the administration period can be 25 days to 30 days, for example.

By applying the method of reducing tobacco addiction in a smoking subject with *Lactobacillus fermentum* GKF3, the smoking amount of the smoking subject is reduced without causing withdrawal symptoms of nicotine, indicating that the oral composition containing *Lactobacillus fermentum* GKF3 is able to reduce tobacco addiction.

BRIEF DESCRIPTION OF THE DRAWINGS

The invention can be more fully understood by reading the followed detailed description of the embodiment, with reference made to the accompanying drawings as follows.

DETAILED DESCRIPTION

Singular forms, "a", "an", and "the", as mentioned in the present invention also cover plural references, unless otherwise stated in the context. A value range (such as 10% to 11% of A) includes its upper and lower limits (i.e., 10%≤A≤11%) if not otherwise stated specially; the value range, for which if no lower limit is defined (such as B lower than 0.2%, or B below 0.2%), can have a lower limit of zero (i.e., 0%≤B≤0.2%). The aforementioned terms are used for illustrating and helping understand the present invention rather than limiting the scope thereof.

As mentioned earlier, the present invention provides a method of reducing tobacco addiction in a smoking subject with *Lactobacillus fermentum* GKF3, in which the method can include but not limited to daily administering to the smoking subject an oral composition containing an effective dosage of *Lactobacillus fermentum* GKF3 as an active ingredient (referred to as GKF3 oral composition).

In one embodiment, the *Lactobacillus fermentum* GKF3 (also called strain GKF3) has been deposited on Jan. 12, 2018 at the China General Microbiological Culture Collection Center (CGMCC, Address: Institute of Microbiology Chinese Academy of Sciences, No. 1, West Beichen Road, Chaoyang District, Beijing 100101, China), with an accession number CGMCC 15203. The deposit was made under the terms of the Budapest Treaty.

Noted that *Lactobacillus fermentum* belongs to gram-positive bacteria of *Lactobacillus*, and is commonly found in the ferments of animals and/or plants, such as sour dough or pickles. In addition, some specific *Lactobacillus fermentum*, such as *Lactobacillus fermentum* GKF3, can be administered (e.g., orally) to animals since the *Lactobacillus fermentum* GKF3 rarely causes side effects under a safe dose.

In one embodiment, the effective dosage of the *Lactobacillus fermentum* GKF3 that the GKF3 oral composition contains can be 700 mg/60 kg bw/day to 900 mg/60 kg bw/day, for example, equivalent to $10^{10}$ CFU/60 kg bw/day to $10^{12}$ CFU/60 kg bw/day. If the effective dosage of the *Lactobacillus fermentum* GKF3 is lower than 700 mg/60 kg bw/day and/or $10^{10}$ CFU/60 kg bw/day, the tobacco addiction can hardly be reduced. If the effective dosage is higher than 800 mg/60 kg bw/day and/or $10^{12}$ CFU/60 kg bw/day, the cost will increase, but the effect of the *Lactobacillus fermentum* on reducing tobacco addiction will not be improved significantly. In one embodiment, by daily administering the oral composition for an administration period, the tobacco addiction can be effectively reduced, in which the administration period can be 25 days to 30 days, for example.

The aforementioned "smoking subject" may interchangeably refer to a current smoker. According to the international definition, the current smoker is one that has smoked over 100 cigarettes (5 packs) up to now and admits tobacco products within 30 days.

One of the technical features of the present invention is that the effect of *Lactobacillus fermentum* GKF3 on reducing tobacco addiction is evaluated by combining objective physiological test values and a subjective cognition scale. In details, the aforementioned "reducing tobacco addiction" objectively refers to reducing a smoking amount (for example, the frequency and/or amount of smoking). On the other hand, the aforementioned "reducing tobacco addiction" subjectively refers to the condition that the smoking subject has no withdrawal symptoms of nicotine when the amount of nicotine in blood of the smoking subject decreases as the smoking amount reduces.

In detail, the smoking amount of the smoking subject can be determined by the nicotine metabolites in the urine, since the nicotine metabolites can be detected in the urine of the smoking subject 7 days to 10 days after a smoking subject smokes, and the total amount of the nicotine metabolites is positively correlated to the smoking amount. Therefore, the smoking amount of the smoking subject is determined to reduce when the total amount of nicotine metabolites in the urine of the smoking subject are reduced by more than a preset concentration, in which the preset concentration is 10 ng/mL. The nicotine metabolites can include but not limited to cotinine and/or trans-3-hydroxycotinine.

As mentioned above, the effect of reducing tobacco addiction can be evaluated by the reduced total amount of nicotine metabolites in the urine of a smoking subject after the smoking subject is daily administered with the GKF3 oral composition. Furthermore, the effect of reducing tobacco addiction can also be evaluated by the percentage of the smoking subjects with reduced tobacco addiction, in which the percentage of the smoking subjects with reduced tobacco addiction is defined as the percentage of the smoking subject numbers having reduced smoking amount over the all smoking subject numbers. The reduced smoking amount refers to a difference by comparison of the total amount of nicotine metabolites in the urine before and after the administration of the GKF3 in the same smoking subject. Typically, more than 10 ng/mL of the difference of the total amount of nicotine metabolites in the urine can be determined as the reduced tobacco addiction of smoking subject.

In one embodiment, the withdrawal symptoms of nicotine can be evaluated by CES-D (the center for epidemiologic studies depression scale) designed by the National Institute of Mental Health, for example. CES-D is a common depression scale for epidemiology, which employs CES-D total scores to quantize the frequency of depressed mood subjectively evaluated by a smoking subject. A smoking subject with a reduced smoking amount is determined to have withdrawal symptoms of nicotine when the smoking subject has an increased CES-D total score. In contrast, the corresponding smoking subject is determined not to have withdrawal symptoms of nicotine when the smoking subject has an increased CES-D total score.

Clinical trials have proved that the *Lactobacillus fermentum* GKF3 reduces 10 ng/mL to 1,100 ng/mL of nicotine metabolites in the urine of a smoking subject daily administered with the *Lactobacillus fermentum* GKF3 for 4 weeks when compared to a corresponding smoking subject not daily administered with the *Lactobacillus fermentum* GKF3. Moreover, the percentage of the smoking subjects having reduced tobacco addiction accounting for the smoking subjects daily administered with the *Lactobacillus fermentum* GKF3 is higher than the percentage of the smoking subjects having reduced tobacco addiction accounting for the smoking subjects not daily administered with the *Lactobacillus fermentum* GKF3, indicating that *Lactobacillus fermentum* GKF3 can objectively reduce tobacco addiction.

In addition, by evaluating with CES-D, the smoking subject daily administered with the *Lactobacillus fermentum* GKF3 is found to have lower CES-D scores when compared to a corresponding smoking subject not daily administered with the *Lactobacillus fermentum* GKF3, indicating the smoking subject daily administered with the *Lactobacillus fermentum* GKF3 has a lower frequency of depressed mood and can be determined to have no withdrawal symptoms of nicotine. Thus, it is proved that the *Lactobacillus fermentum* GKF3 can subjectively reduce tobacco addiction. To sum up, *Lactobacillus fermentum* GKF3 can reduce the smoking amount of the smoking subject without producing the withdrawal symptoms of nicotine, indicating that *Lactobacillus fermentum* GKF3 has an effect of reducing tobacco addiction.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the followed claims.

Example 1. Strain Source and Preparation

The fermented pickles commercially available in Beipu, Hsinchu, Taiwan (ROC) were diluted with 10 volumes of water, followed by homogenization to obtain a homogeneous mixture. Then, 1 mL of the homogeneous mixture was inoculated into an MRS culture solution containing 0.1% of bromocresol green for an incubation at 37° C. for 16 hours to obtain a culture solution, thereby screening out strains (including *Lactobacillus*) preferring to grow in a weak acid (with pH of 6.5±0.2) environment. The culture solution was serially diluted and then respectively spread on 5 solid culture media (including: a Rogosa agar medium, a bidobacterium iodoacetate medium 25 (BIM-25), an agar medium containing potato starch and yeast extract, a bromocresol green MRS agar medium and a bromocresol purple MRS agar medium), followed by an incubation at 37° C. for 40 hours to obtain single colonies. First screened strains were obtained by picking 15 to 20 single colonies from each solid culture medium.

Next, strains with an anti-inflammation effect were screened out by using the lipopolysaccharide treated RAW 264.7 macrophage (referred to as model cell herein) as a cellular inflammatory reaction model. A strain was determined to have the anti-inflammation effect when the secretion amounts of nitric oxide and tumor necrosis factor (TNF)-α of the model cell administered with the strain was reduced by 80% compared to that of the model cell not administered with the strain. Then, strain GKF3 with tryptophan decarboxylase activity was screen out from the strains with the anti-inflammation effect.

After the genomic DNA (gDNA) of the strain GKF3 was purified, a polymerase chain reaction (PCR) was performed with an upstream primer with a nucleic acid sequence shown in SEQ ID NO: 1 and a downstream primer with a nucleic acid sequence shown in SEQ ID NO: 2 to obtain a DNA fragment of the recN gene with a nucleic acid sequence shown in SEQ ID NO: 3. By sequence alignment, the strain GKF3 was identified as *Lactobacillus fermentum*.

The *Lactobacillus fermentum* GKF3 was deposited on Jan. 12, 2018 at the China General Microbiological Culture Collection Center (Address: No. 1, West Beichen Road, Chaoyang District, Beijing, China 100101, China), with an accession number CGMCC 15203. The deposit was made under the terms of the Budapest Treaty. The *Lactobacillus fermentum* strain GKF3 was also deposited on Feb. 12, 2018 at the Bioresource Collection and Research Center (Address: No. 331, Food Road, East Hsinchu, Taiwan 30062) of Taiwan Food Industry Development Research Institute with an accession number BCRC 910824.

The *Lactobacillus fermentum* GKF3 was inoculated into an MRS agar medium, followed by a solid culture step to obtain single colonies. Then, the single colonies were inoculated into a fermentation substrate and subjected to a fermentation step for 18 hours to obtain a ferment product. The solid culture step was performed at a temperature of 37° C. The fermentation step was performed at a condition of a temperature of 37° C., a ventilation capacity of 0.5 air volume/culture volume/min (vvm) of carbon dioxide and an oscillation rate of 500 rpm. The formula of the fermentation substrate was shown in Table 1.

TABLE 1

| Component | Weight percentage |
|---|---|
| Glucose | 1-10% |
| Yeast extract | 0.1-5% |
| Peptone | 0.1-5% |
| Trace element | 0.01-2% |
| Cysteine | 0.01-0.1% |
| TWEEN-80 | 0.05-1% |

The ferment product was centrifuged at a speed of 10,000 rpm to obtain a bacterial pellet. Then, the bacterial pellet was mixed with 20 weight % of skim milk powder, and the mixture was subjected to lyophilization to obtain a GKF3 lyophilized powder. The lyophilization was well-known and could be adjusted without affecting the following evaluation, and thus would not be elaborated herein.

Example 2. Evaluation of the Effect of Lactobacillus fermentum GKF3 on Reducing Tobacco Addiction by Using Physiological Test Values The GKF3 lyophilized powder was embedded into capsules to obtain capsules of the bacterial powder of Lactobacillus fermentum GKF3, in which each of the capsules of the bacterial powder of Lactobacillus fermentum GKF3 contained 400 mg of the lyophilized powder of GKF3, which was equivalent to $5 \times 10^9$ CFU of viable Lactobacillus fermentum GKF3. Then, microcrystalline α-cellulose was embedded into capsules, to obtain placebo capsules.

Subjects were recruited, in which the subjects were smoking subjects aged 20 to 50 healthy young males without critical illness. It was worth noting that those conforming to any one of the following situations were excluded from the subjects:
(1) who suffered from a critical mental illness;
(2) who took antibiotics;
(3) who had a high level of alcohol addiction or other behavior that could influence the experimental results;
(4) who continued the psychotropic medication (for example, taking anti-depression drugs);
(5) who had or continued a nicotine related replacement therapy; and
(6) who ever took probiotics in last three months or continued taking probiotics at that time.

In addition, during the evaluation trial, the following described subjects should drop out of the trial: the subject who felt uncomfortable with the reagent (here, referring to the capsules of the bacterial powder of Lactobacillus fermentum GKF3 and/or placebo capsules); the subject who refused to use the reagent as required or refused to live daily under the regulation of the evaluation trial, and thus caused an incompletion of the data, failures of judging the reagent effect and/or failures of evaluating effect or safety; the subject who got a disease or took a drug or health food which influenced the experimental results during the evaluation trial; the subject who refused to participate in the urine test and/or the subject who could not finish CES-D.

The subjects (n=45) were randomly divided into a first group (n=23) and a second group (n=22), in which there were no statistically significant differences between the parameters of blood biochemical values the first group and the second group. Please refer to FIG. 1 and FIG. 2, in which FIG. 1 was a flow chart illustrating an experiment of the first group according to an embodiment of the present invention and FIG. 2 was a flow chart illustrating an experiment of the second group according to an embodiment of the present invention. In the following process 100 and process 200, a urine test was performed by detecting the total amount of nicotine metabolites in the urine, in which the nicotine metabolites included cotinine and/or trans-3-hydroxycotinine. The detection method of cotinine and/or trans-3-hydroxycotinine was an ordinary skill for a person skilled in the art and could be adjusted without affecting the results of the evaluation trial, and thus would not be elaborated herein. A control treatment was performed by administering 2 placebo capsules to the subject after breakfast every day. The experimental treatment was performed by administering 2 capsules of the bacterial powder of Lactobacillus fermentum GKF3 to the subject after breakfast every day. Specifically, during the process 100 and process 200, the subjects could smoke at will and/or as the subject wish.

Figure 1:
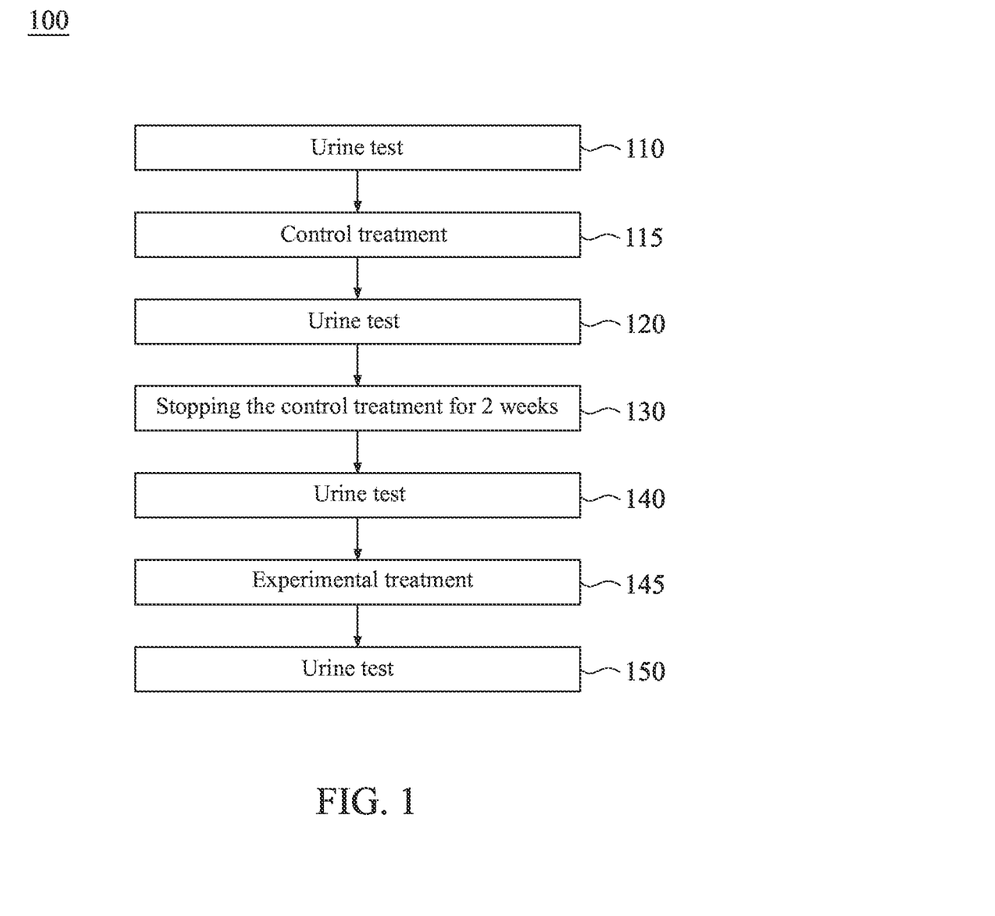
FIG. 1 was a flow chart illustrating an experiment of the first group according to an embodiment of the present invention.

Please refer to the process 100 of FIG. 1. As shown in step 110, the urine test was performed. Next, the control treatment was performed for 4 weeks, and then the urine test was performed again, as shown in step 115 and step 120. Then, the control treatment was stopped for 2 weeks according to step 130. Next, as shown in step 140, the urine test was performed. Then, the experimental treatment was performed for 4 weeks, and then the urine test was performed again, as shown in step 145 and step 150. The trial lasted for 10 weeks in total.

Figure 2:
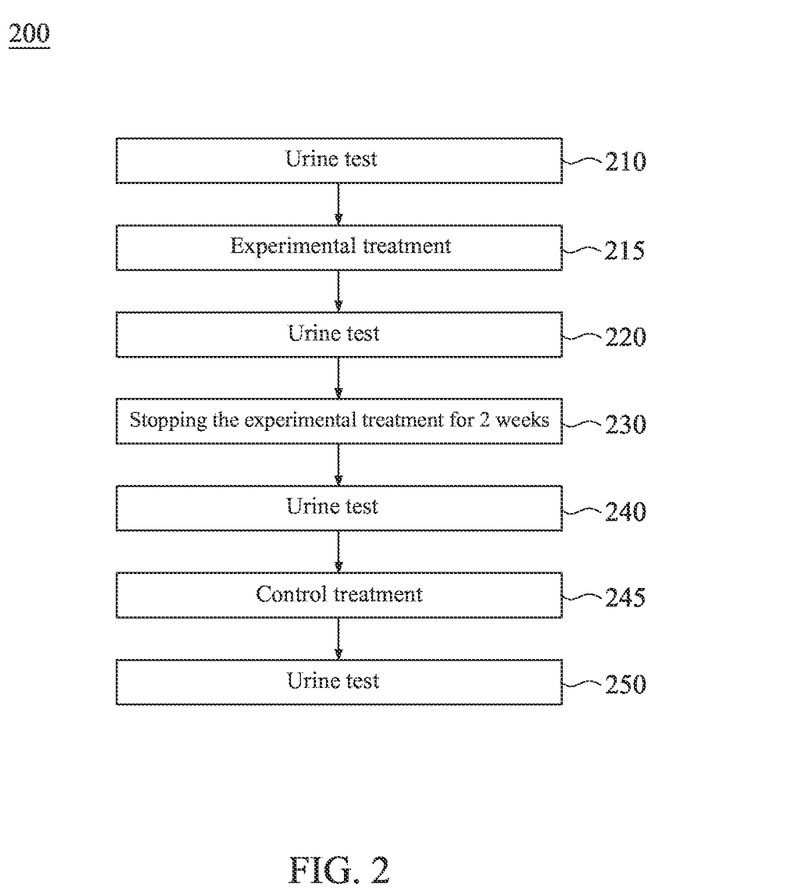
FIG. 2 was a flow chart illustrating an experiment of the second group according to an embodiment of the present invention.

Please refer to the process 200 of FIG. 2. As shown in step 210, the urine test was performed. Next, the experimental treatment was performed for 4 weeks, and then the urine test was performed again, as shown in step 215 and step 220. Then, the experimental treatment was stopped for 2 weeks according to step 230. Next, as shown in step 240, the urine test was performed. Then, the control treatment was performed for 4 weeks, and then the urine test was performed again, as shown in step 245 and step 250. The trial lasted for 10 weeks in total.

The process 100 and process 200 were designed as a crossover trial, which had an advantage to obtain the evaluation results of the control treatment (control treatment group) and the experimental treatment (experimental treatment group) from the same subject, and thus could reduce the number of the required subjects. The average total amount of nicotine metabolites in urine of the subjects before and after different treatments were recorded in Table 2.

TABLE 2

| Average total amount of nicotine metabolites in urine (ng/mL) | Before | After |
|---|---|---|
| Control treatment | 3030.5 | 4441.8 |
| Experimental treatment | 3701.1 | 2653.4 |

As shown in Table 2, the average total amount of nicotine metabolites in the urines of the subjects subjected to the experimental treatment was 1,047.7 ng/mL lower than that of the subjects before subjected to the experimental treatment. However, the average total amount of nicotine metabolites in the urines of the subjects subjected to the control treatment was higher than that of the subjects before subjected to the control treatment. Accordingly, the subject daily administered with Lactobacillus fermentum GKF3 had lower total amount of nicotine metabolites in urine, indicating a reduced smoking amount of the subject. Thus, the Lactobacillus fermentum GKF3 was proved to be able to reduce tobacco addiction.

The percentage of the subjects with reduced tobacco addiction in the experimental treatment group was obtained by calculating the percentage of the subjects whose total amount of the nicotine metabolites in the urine reduced more than 10 ng/mL after the subjects were subjected to the experimental treatment over all the subjects. Similarly, the percentage of the subjects with reduced tobacco addiction in the control treatment group was obtained by calculating the percentage of the subjects whose total amount of the nicotine metabolites in the urine was reduced by more than 10 ng/mL after the subjects were subjected to the control treatment over all the subjects.

Figure 3:
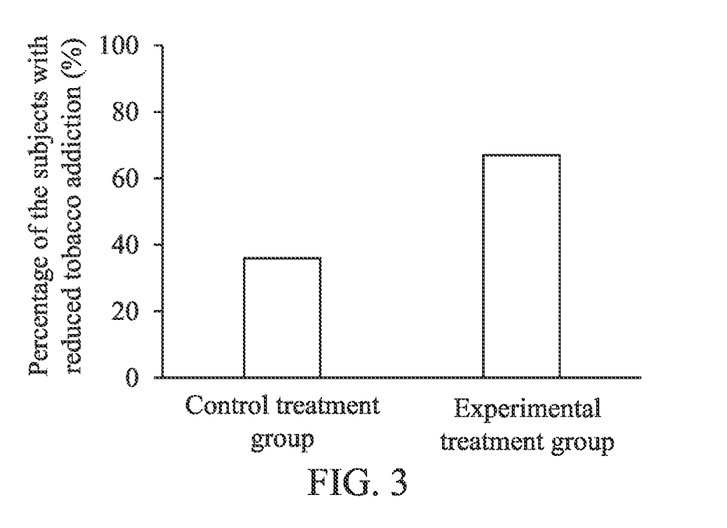
FIG. 3 was a bar char illustrating the percentage of the subjects with reduced tobacco addiction in different treatment groups according to an embodiment of the present invention.

FIG. 3 was a bar char illustrating the percentage (%) of the subjects with reduced tobacco addiction in different treatment groups according to an embodiment of the present invention, in which the horizontal axis showed the control treatment group and the experimental treatment group respectively from left to right, and the longitudinal axis showed the percentage of the subjects with reduced tobacco addiction (unit: %). As shown in FIG. 3, the percentage of the subjects with reduced tobacco addiction in the experimental treatment group was 67% (30/45 subjects), which was 31% higher than that (36%, 16/45 subjects) of the subjects in the control treatment group, proving that the *Lactobacillus fermentum* GKF3 reduces the tobacco addiction.

Example 3. Evaluation of the Effect of *Lactobacillus fermentum* GKF3 in Reducing Tobacco Addiction by Using a Cognition Scale With the cognition scale CES-D, the subjects were allowed to subjectively evaluate the frequency of depression symptoms within 1 week. The scores 0, 1, 2 and 3 given by the subject indicated that the frequency was zero, rare (less than 1 day every week), sometimes (1 day to 2 days every week) and often (3 days to 7 days every week), respectively. The depression symptoms included 20 symptoms such as depressed mood, guilt and worthlessness, feelings of helplessness and hopelessness, psychomotor retardation, loss of appetite and sleep disturbance, and thus the CES-D total scores were between 0 and 60. The subject was determined to have withdrawal symptoms of nicotine when the CES-D total scores of the subject increased significantly as the smoking amount reduced.

The subjects of the first group finished CES-D before step 115 (week 0 of the trial), after step 115 (week 4 of the trial) and after step 145 (week 10 of the trial) in the process 100. The subjects of the second group finished CES-D before step 215 (week 0 of the trial), after step 215 (week 4 of the trial) and after step 245 (week 10 of the trial) in the process 200. The CES-D total scores of the subjects of the first group and second group were shown in FIG. 4, which was a bar chart illustrating the CES-D total scores of the subjects at different times according to an embodiment of the present invention, in which the horizontal axis represented the week, the longitudinal axis represented the CES-D total scores, the bar 401 represented the control treatment group, and the bar 403 represented the experimental treatment group. It should be noted that the bar 401 represented the subjects of the first group in week 0 and week 4, but represented the subjects of the second group in week 10. On the contrary, the bar 403 represented the subjects of the second group in week 0 and week 4, but represented the subjects of the first group in week 10.

Figure 4:
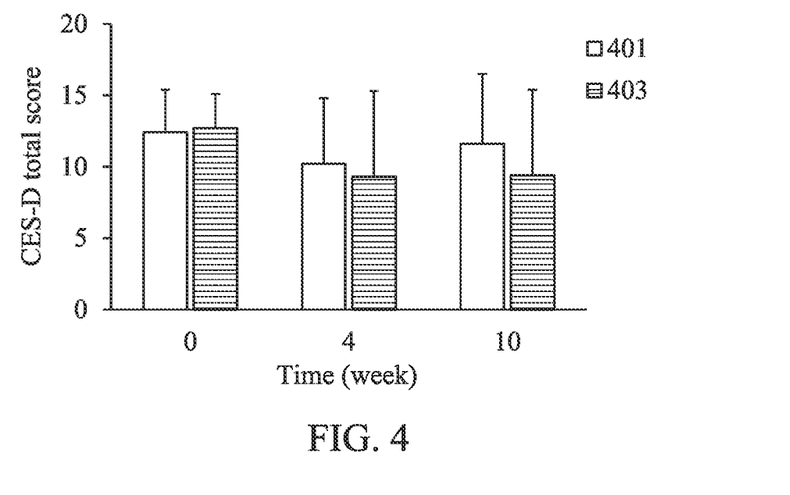
FIG. 4 was a bar chart illustrating the CES-D total scores of the subjects at different times according to an embodiment of the present invention.

As shown in FIG. 4, the averages±standard deviations of the CES-D total scores of the subjects of the first group were 12.4±3 (bar 401) on week 0, 10.2±4.6 (bar 401) on week 4 (after the control treatment) and 9.4±6 (bar 403) on week 10 (after the experimental treatment). The averages±standard deviations of the CES-D total scores of the subjects of the second group were 12.4±3 (bar 403) on week 0, 10.2±4.6 (bar 403) on week 4 (after the experimental treatment), and 11.6±4.9 (bar 401) on week 10 (after the control treatment).

As FIG. 4 showed, the CES-D total scores of the subjects of the first group reduced after the subjects were subjected to the experimental treatment (bar 403 on week 10) compared to that of the subject not subjected to the experimental treatment (bar 401 on week 4). On the other hand, the CES-D total scores of the subjects of the second group reduced after the subject were subjected to the experimental treatment (bar 403 on week 10) compared to that of the subjects not subjected to the experimental treatment (bar 403 on week 4). Referred to both FIG. 3 and FIG. 4, the smoking amounts of the subjects reduced after the subject were subjected to the experimental treatment, indicating that the *Lactobacillus fermentum* GKF3 could not only reduce the smoking amount of the subject, but also prevent the withdrawal symptoms of nicotine. Moreover, the *Lactobacillus fermentum* GKF3 had the tendency to reduce the frequency of the depression symptoms, thereby proving that the *Lactobacillus fermentum* GKF3 was able to reduce the tobacco addiction.

In conclusion, the aforementioned specific manufacturing processes, specific administration modes, specific subjects and specific evaluation methods are only intended to illustrate and describe method of reducing tobacco addiction in a smoking subject with *Lactobacillus fermentum* GKF3 of the present invention. However, those skilled in the art should understand that other manufacturing processes, other administration modes, other subjects and other evaluation methods, not limited to the above, can also be used for describing the method of reducing tobacco addiction in a smoking subject with *Lactobacillus fermentum* GKF3 of the present invention without departing from the spirit and scope of the present invention. For example, other manufacturing processes, other administration modes, other subjects and other evaluation methods can be used on the premise of not influencing the effect of *Lactobacillus fermentum* GKF3 in reducing tobacco addiction.

It can be seen from the aforementioned embodiments that the method of reducing tobacco addition with the *Lactobacillus fermentum* GKF3 in a smoking subject of the present invention has the advantages of using probiotics to reduce tobacco addiction without providing nicotine, thereby rarely causing side effects. Thus, the oral composition containing the *Lactobacillus fermentum* GKF3 can be used as a food product and/or a medicine product to assist smoking cessation.

Although the present invention has been described in considerable detail with reference to certain embodiments thereof, other embodiments are possible. Therefore, the spirit and scope of the appended claims should not be limited to the description of the embodiments contained herein.

The invention claimed is:

1. A method of reducing tobacco addiction in a smoking subject comprising daily administering to the smoking subject an oral composition consisting of an effective dosage of *Lactobacillus fermentum* GKF3 as an active ingredient, wherein the *Lactobacillus fermentum* GKF3 is deposited in China General Microbiological Culture Collection Center (CGMCC) with an accession number CGMCC 15203 on Jan. 12, 2018, the smoking subject excludes one taking a nicotine related replacement therapy, and a total amount of nicotine metabolites is reduced by 10 ng/mL to 1,100 ng/mL in urine of the smoking subject daily administered with the oral composition when compared to a corresponding smoking subject not administered with the oral composition.

2. The method of claim 1, wherein the effective dosage is 700 mg/60 kg body weight (bw)/day to 900 mg/60 kg bw/day.

3. The method of claim 1, wherein the effective dosage is $10^{10}$ colony forming unit (CFU)/60 kg bw/day to $10^{12}$ CFU/60 kg bw/day.

4. The method of claim 1, wherein the nicotine metabolites comprise cotinine and/or trans-3-hydroxycotinine.

5. The method of claim 1, wherein the oral composition is daily administered to the smoking subject for an administration period of 25 days to 30 days.

6. A method of reducing tobacco addiction in a smoking subject comprising daily administering to the smoking subject an oral composition consisting of an effective dosage of Lactobacillus fermentum GKF3 as an active ingredient, wherein an accession number of the Lactobacillus fermentum GKF3 is CGMCC 15203, the effective dosage is 700 mg/60 kg bw/day to 900 mg/60 kg bw/day, the smoking subject excludes one taking a nicotine related replacement therapy, and a total amount of nicotine metabolites is reduced by 10 ng/mL to 1,100 ng/mL in urine of the smoking subject administered with the oral composition when compared to a corresponding smoking subject not administered with the oral composition.

7. The method of claim 6, wherein the nicotine metabolites comprise cotinine and/or trans-3-hydroxycotinine.

8. The method of claim 6, wherein the oral composition is daily administered to the smoking subject for an administration period of 25 days to 30 days.

9. A method of reducing tobacco addiction in a smoking subject comprising daily administering to the smoking subject an oral composition consisting of an effective dosage of Lactobacillus fermentum GKF3 as an active ingredient, wherein an accession number of Lactobacillus fermentum GKF3 is CGMCC 15203, the effective dosage is $10^{10}$ CFU/60 kg bw/day to $10^{12}$ CFU/60 kg bw/day, the smoking subject excludes one taking a nicotine related replacement therapy, and a total amount of nicotine metabolites is reduced by 10 ng/mL to 1,100 ng/mL in urine of the smoking subject administered with the oral composition when compared to a corresponding smoking subject not administered with the oral composition.

10. The method of claim 9, wherein the nicotine metabolites comprise cotinine and/or trans-3-hydroxycotinine.

11. The method claim 9, wherein the oral composition is daily administered to the smoking subject for an administration period.

12. The method claim 9, wherein an administration period is 25 days to 30 days.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Upstream primer

<400> SEQUENCE: 1
atccaaggtc aaaatgagca                                           20

<210> SEQ ID NO 2
<211> LENGTH: 20
<212> TYPE: DNA
<213> ORGANISM: Artificial Sequence
<220> FEATURE:
<223> OTHER INFORMATION: Downstream primer

<400> SEQUENCE: 2
cttcaacccg ttggttagtg                                           20

<210> SEQ ID NO 3
<211> LENGTH: 1071
<212> TYPE: DNA
<213> ORGANISM: Lactobacillus fermentum GKF3

<400> SEQUENCE: 3
taacgctaag gttcagcccc tactagcgtc gtaccaagag cagtaccaag agtaccggcg      60
tttggaggcg gcggttaacc aaaagaaggc caacgagcaa cagtgggccc agcgcctcga    120
catgttgcgc taccaagtta aagaaattgg tgacgccgac ttgcgggccg acgaagaaga    180
tgaattaatc gccgaacgtg agcgactgga acacttccaa cagattgcca ccaccctcca    240
gcaggtggtt ggggtgttga acgatgacga agaggcgcct gtcttagacc aggtcgccac    300
catcatgaat gcagcccaag agattgcgcc cttcgatccc gaatacgatg acctggccca    360
gtcccttcct gacgcctact attcactgca agacgtttcc aaccaagctg gccaccagtt    420
ggatagcctc gagtttgatg aggagcgact ggccacgatc aacgcccgct tagcgacgat    480
tgccgacttg gagcacaagt atggtgaaag cttagccgac gttttggcgt actacgacca    540
gatcaaagaa gagcttaccg atatggaggc cgcggccgat tcaggttccg atttggaaga    600
gcggttaaat gcggtccagg ccgatttgtt aaaccaaggg aacgccctga gccaagtgcg    660
gcaaacggcg gcccgcaaat tagccaagca ggttcacacc caactaaagg aactgtacat    720
ggataaggcg gtttttgaag tgaactttgc caaaaccaag aagccggtct tctctgccac    780
cgggatcgat caggttgaat tctacattca aaccaatcct ggtgaggcaa tgggacccctt    840 ggcccggatc gcctccgggg gggaactttc ccgggtgatg ctggccttaa agacgatctt    900
tgcccagggc gaagggggtta caagcatcat ctttgacgaa gtcgatactg gggtttccgg    960
gcgggtcgcc caagccattg ccgataagat tcgcttgatt gccgagggct cacaggtcct   1020
ttgcattact cacttaccac aggtggcagc ggttgcccaa caccacctct t             1071